US00PP20532P2

(12) United States Plant Patent
Hanes

(10) Patent No.: US PP20,532 P2
(45) Date of Patent: Dec. 8, 2009

(54) ***PELARGONIUM* PLANT NAMED 'CLIP VELRED'**

(50) Latin Name: *Pelargonium hortorum*
Varietal Denomination: Clip Velred

(75) Inventor: Mitchell Hanes, Morgan Hill, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 12/228,620

(22) Filed: Aug. 14, 2008

(51) Int. Cl.
*A01H 5/00* (2006.01)

(52) U.S. Cl. ..... Plt./330

(58) Field of Classification Search ..... Plt./330
See application file for complete search history.

*Primary Examiner*—Annette H Para
(74) *Attorney, Agent, or Firm*—S. Matthew Edwards

(57) ABSTRACT

A new *Pelargonium* plant named 'Clip Velred,' particularly distinguished by the velvety red flowers, dark foliage, medium vigor, and good branching.

1 Drawing Sheet

Latin name of the genus and species of the plant claimed: *Pelargonium hortorum.*

Varietal denomination: 'Clip Velred'.

BACKGROUND OF THE NEW PLANT

The present invention comprises a new *Pelargonium,* botanically known as *Pelargonium hortorum,* and hereinafter referred to by the variety name 'Clip Velred.'

'Clip Velred' is a product of a planned breeding program. The new cultivar 'Clip Velred' has velvety red flowers, dark foliage, medium vigor, and good branching 'Clip Velred' originated from a hybridization in a controlled breeding program in Gilroy, Calif. USA. The female parent was an unpatented hybrid seedling identified as '10080-4' with orange/scarlet flower color. '10080-4' has single flowers and is later to bloom than 'Clip Velred.'

The male parent of 'Clip Velred' was an unpatented hybrid seedling identified as '10073-3.' '10073-3' has a dark red flower color, a green leaf, and larger plant habit than 'Clip Velred.'

'Clip Velred' was selected as one flowering plant within the progeny of the stated cross in 2005 in a controlled environment in Gilroy, Calif. USA.

The first act of asexual reproduction of 'Clip Velred' was accomplished when vegetative cuttings were taken from the initial selection in November 2005 in a controlled environment in Gilroy, Calif. USA.

Horticultural examination of plants grown from cuttings of the plant initiated in November of 2005 in Gilroy, Calif. USA, and continuing thereafter, has demonstrated that the combination of characteristics as herein disclosed for 'Clip Velred' are firmly fixed and are retained through successive generations of asexual reproduction.

'Clip Velred' has not been observed under all possible environmental conditions. The phenotype may vary significantly with variations in environment such as temperature, light intensity and day length.

Plant Breeder's Rights for this cultivar were applied for in Canada on Aug. 23, 2007 and in Germany on Jul. 2, 2007. A United States provisional application was applied for on Nov. 15, 2007 and assigned Ser. No. 60/988,364. The title of the application was "Flower Pigmentation in *Pelargonium hortorum*." 'Clip Velred' has not been made publicly available more than one year prior to the filing of this application.

BRIEF DESCRIPTION OF THE NEW VARIETY

The accompanying photographic drawing shows typical flower and foliage characteristics of 'Clip Velred' with colors being as true as possible with an illustration of this type. The photographic drawing shows a container of three flowering potted plants of the new variety, and a close-up of the flowers. The whole plant photograph was taken in July 2008 and the close-up was taken in the spring of 2007 both in Gilroy, Calif. USA. Both were grown in Gilroy, Calif. USA and were approximately 3–4 months old.

DETAILED BOTANICAL DESCRIPTION

The measurements were taken in Gilroy, Calif. USA, in August 2007 on plants that were growing in a 14 inch container, containing three flowering plants. Culture of these plants started approximately in April 2007 in a greenhouse and then transferred to an outdoors trial in June. The plants were approximately 4 months old.

Color chart used: The Royal Horticultural Society Colour Chart (R.H.S.) 2001

BRIEF SUMMARY OF INVENTION

The following observations, measurements, and comparisons describe plants grown outside in Gilroy, Calif. USA. The following traits have been repeatedly observed and are determined to be basic characteristics of the new variety. The combination of these characteristics distinguishes this *Pelargonium* as a new and distinct variety.

TABLE 1

DIFFERENCES BETWEEN THE NEW VARIETY AND A SIMILAR VARIETY

| | 'Clip Velred' | 'Clips Dared' (U.S. Plant Pat. No. 16,595) |
|---|---|---|
| Flower color | Darker red | Lighter red |
| Flowering response | Earlier to flower | Later to flower |
| Peduncle length | Longer | Shorter |
| Vigor | More vigor | Less vigor |

Plant:

*Form, growth and habit.*—Upright, and rounded growth habit, and well branched.

*Plant height.*—12–14 cm.

*Plant height* (*inflorescence included*).—24–26.3 cm.

*Plant width.*—18–20 cm.

Foliage:

*Arrangement.*—Alternate, simple.

*Immature, leaf color, upper surface.*—RHS 137A Lower surface: RHS 137C.

*Mature, leaf color, upper surface.*—RHS 147A Lower surface: RHS 137C.

*Length.*—3.4–3.6 cm.

*Width.*—5.9–6.1 cm.

*Shape.*—Orbicular.

*Base shape.*—Reniform.

*Apex shape.*—Rounded to slightly mucronulate.

*Margin.*—Irregularly crenate.

*Texture.*—Hirsute; glandular hairs on both sides.

*Color of zone.*—Very light hue of RHS 176B.

*Color of veins, upper surface.*—Indistinct.

*Color of veins, lower surface.*—RHS 144B but a little darker.

*Petioles color.*—RHS 144B but a little darker.

*Petioles length.*—7.5 cm.

*Diameter of petiole.*—0.2 cm.

*Texture.*—Slightly hirsute; glandular hairs.

Stem:

*Color of stem.*—RHS 144A.

*Length of stem.*—8–10 cm.

*Diameter.*—0.7–0.8 cm.

*Length of internodes.*—1.0–3.0 cm.

*Texture.*—Slightly hirsute; glandular hairs.

Inflorescence:

*Type.*—An umbel composed of 25–30 flowers and buds.

*Umbel diameter.*—10–12 cm.

*Umbel depth.*—6–7 cm.

*Color of peduncle.*—RHS 144A with anthocyanin overlay of RHS 177B maturing to about RHS 183B.

*Length of peduncle.*—15–19 cm.

*Peduncle diameter.*—0.4 cm.

*Texture.*—Slightly hirsute; short glandular hairs.

*Pedicel color.*—RHS 144A with anthocyanin overlay of RHS 177A.

*Length of pedicel.*—2.5–3.8 cm.

*Diameter of pedical.*—0.15 cm.

*Texture.*—Slight hirsute; short glandular hairs some with approximately RHS 25B.

Corolla:

*Form.*—Polypetalous, mostly overlapping, but some flowers have gaps.

*Number of petals.*—5–6.

*Width of flower.*—4.5–5.0 cm.

*Color upper petals, upper surface.*—Closest to RHS 46B but more velvety bluish-red with a lighter red hue mid petal; RHS 187A veins, more heavily basally.

*Color upper petals, lower surface.*—Between RHS 53B–C.

*Length of upper petals.*—2.4–2.5 cm.

*Width of upper petals.*—1.7–1.8 cm.

*Color lower petals, upper surface.*—Closest to RHS 46B but more velvety bluish-red; RHS 187A veins.

*Color lower petals, lower surface.*—Between RHS 53B–C.

*Length of lower petals.*—2.3–2.4 cm.

*Width of lower petals.*—1.8 cm.

*Petal shape.*—Obovate.

*Apex shape.*—Rounded.

*Margin.*—Entire.

*Petal texture.*—Papillose.

*Number of petaloids.*—2–3.

*Color of petaloids.*—Same as lower petals.

*Duration of flowering.*—Continuous flowering throughout the Summer.

Bud (just before opening):

*Color.*—Closest to RHS 46A.

*Length.*—1.4–1.5 cm.

*Width.*—0.6–0.7 cm.

*Shape.*—Elliptical.

*Number of sepals.*—5, fused at the base.

*Color of sepals.*—RHS 146B with anthocyanin overlay of RHS 187C.

*Length of sepals.*—1.1–1.3 cm.

*Width of sepals.*—0.3–0.4 cm.

*Sepal shape.*—Lanceolate.

*Apex shape.*—Acute.

*Margins.*—Entire.

*Texture.*—Hirsute; glandular hairs.

Reproductive organs:

*Pistil.*—1.

*Length.*—0.8–0.9 cm.

*Style color.*—RHS 61B.

*Style length.*—0.2 cm.

*Stigma color.*—RHS 184B.

*Number of anthers.*—5–6.

*Length filaments.*—0.7–0.8 cm.

*Color of filaments.*—RHS N155B but whiter.

*Pollen amount.*—Moderate.

*Color of pollen.*—RHS N172A.

*Fertility/seed set.*—Not observed on this hybrid.

Disease/pest resistance: Disease resistance and/or susceptibility has not been observed on this hybrid.

What is claimed is:

1. A new and distinct variety of *Pelargonium* plant named 'Clip Velred,' substantially as illustrated and described herein.

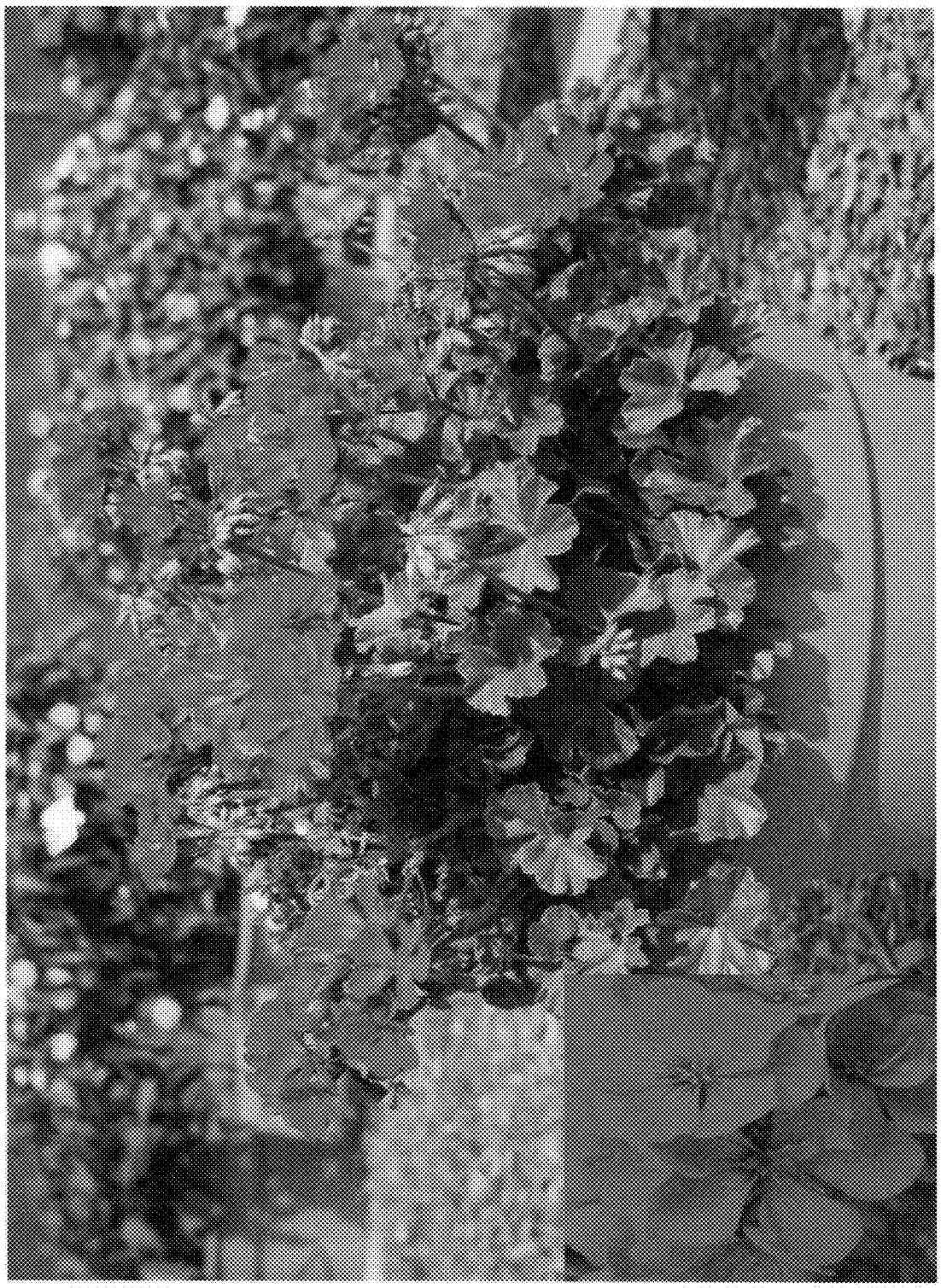

* * * * *